US012677863B2

(12) United States Patent
McNeal et al.

(10) Patent No.: US 12,677,863 B2
(45) Date of Patent: Jul. 14, 2026

(54) INHALABLE COMPOSITIONS COMPRISING CAFFEINE, METHODS OF USE AND AN APPARATUS FOR USING THE SAME

(71) Applicant: Ahkeo Ventures LLC, Irving, TX (US)

(72) Inventors: Kelly McNeal, Irving, TX (US); Brent Skoda, Irving, TX (US)

(73) Assignee: Ahkeo Ventures LLC

( * ) Notice: Subject to any disclaimer, the term of this patent is extended or adjusted under 35 U.S.C. 154(b) by 0 days.

(21) Appl. No.: 18/231,100

(22) Filed: Aug. 7, 2023

(65) Prior Publication Data

US 2024/0215633 A1     Jul. 4, 2024

Related U.S. Application Data

(63) Continuation of application No. 16/859,241, filed on Apr. 27, 2020, now abandoned, which is a continuation of application No. 15/957,199, filed on Apr. 19, 2018, now Pat. No. 10,632,266, which is a continuation of application No. 14/327,137, filed on Jul. 9, 2014, now abandoned.

(Continued)

(51) Int. Cl.
| | |
|---|---|
| *A24B 15/167* | (2020.01) |
| *A24F 40/10* | (2020.01) |
| *A24F 40/42* | (2020.01) |
| *A24F 40/50* | (2020.01) |
| *A61K 9/00* | (2006.01) |
| *A61K 31/522* | (2006.01) |
| *A61K 45/06* | (2006.01) |
| *A61K 47/10* | (2017.01) |
| *A61M 11/04* | (2006.01) |
| *A61M 15/06* | (2006.01) |

(52) U.S. Cl.
CPC ............ *A24B 15/167* (2016.11); *A61K 9/007* (2013.01); *A61K 31/522* (2013.01); *A61K 45/06* (2013.01); *A61K 47/10* (2013.01); *A61M 11/042* (2014.02); *A61M 15/06* (2013.01); *A24F 40/10* (2020.01); *A24F 40/42* (2020.01); *A24F 40/50* (2020.01)

(58) Field of Classification Search
None
See application file for complete search history.

(56) References Cited

U.S. PATENT DOCUMENTS

| | | | |
|---|---|---|---|
| 7,078,016 | B2 | 7/2006 | Rabinowitz |
| 9,186,350 | B2 | 11/2015 | Blackman |

(Continued)

FOREIGN PATENT DOCUMENTS

| | | | |
|---|---|---|---|
| DE | 20 2010 010 189 U1 | 10/2010 | |
| EP | 2 113 178 A1 | 11/2009 | |

(Continued)

OTHER PUBLICATIONS

International Preliminary Report on Patentability for International Application No. PCT/US2014/045981 dated Jan. 12, 2016, 7 pages.

(Continued)

*Primary Examiner* — Dennis R Cordray
(74) *Attorney, Agent, or Firm* — Foley & Lardner LLP

(57) ABSTRACT

Described herein are compositions, methods and an apparatus relating to the pulmonary delivery of an inhalable composition comprising caffeine, or a salt thereof, and a solvent selected from the group consisting of propylene glycol, glycerol, ethanol and a combination thereof.

10 Claims, 2 Drawing Sheets

100

102

104

Related U.S. Application Data

(60) Provisional application No. 61/844,772, filed on Jul. 10, 2013.

(56) References Cited

U.S. PATENT DOCUMENTS

| | | | |
|---|---|---|---|
| 10,632,266 | B2 | 4/2020 | McNeal et al. |
| 2005/0281772 | A1 | 12/2005 | Bromley et al. |
| 2006/0018839 | A1 | 1/2006 | Leni et al. |
| 2006/0171938 | A1 | 8/2006 | Stock et al. |
| 2009/0018136 | A1 | 1/2009 | Oppenheimer et al. |
| 2010/0236562 | A1 | 9/2010 | Hearn et al. |
| 2011/0015154 | A1 | 1/2011 | Kellermann et al. |
| 2011/0036346 | A1 | 2/2011 | Cohen et al. |
| 2011/0304282 | A1 | 12/2011 | Li et al. |
| 2013/0310422 | A1 | 11/2013 | Brown et al. |
| 2014/0144429 | A1 | 5/2014 | Wensley et al. |
| 2014/0261474 | A1 | 9/2014 | Gonda |
| 2016/0038552 | A1 | 2/2016 | Bredesen et al. |
| 2016/0194368 | A1 | 7/2016 | Hoge et al. |
| 2017/0368012 | A1 | 12/2017 | Zemel et al. |

FOREIGN PATENT DOCUMENTS

| | | |
|---|---|---|
| WO | WO-00/64448 A1 | 11/2000 |
| WO | WO-03/057188 A1 | 7/2003 |

OTHER PUBLICATIONS

International Search Report and Written Opinion for Application No. PCT/US2014/045981 dated Oct. 28, 2014.

Non-Final Office Action on U.S. Appl. No. 16/859,241 DTD Feb. 7, 2023.

Notice of Allowance on U.S. Appl. No. 15/957,199 DTD Jan. 2, 2020.

Notice of Allowance on U.S. Appl. No. 15/957,199 DTD Aug. 28, 2019.

US Office Action on U.S. Appl. No. 14/327,137 dated Oct. 19, 2016, 18 pages.

100

102

104

INHALABLE COMPOSITIONS COMPRISING CAFFEINE, METHODS OF USE AND AN APPARATUS FOR USING THE SAME

CROSS-REFERENCE TO RELATED APPLICATIONS

This patent application is a continuation of, and claims priority to and the benefit of U.S. patent application Ser. No. 16/859,241, titled "INHALABLE COMPOSITIONS COMPRISING CAFFEINE, METHODS OF USE AND AN APPARATUS FOR USING THE SAME," and filed Apr. 27, 2020, which is a continuation of, and claims priority to and the benefit of U.S. patent application Ser. No. 15/957,199, titled "INHALABLE COMPOSITIONS COMPRISING CAFFEINE, METHODS OF USE AND AN APPARATUS FOR USING THE SAME," and filed Apr. 19, 2018, which is a continuation of, and claims priority to and the benefit of U.S. patent application Ser. No. 14/327,137, titled "INHALABLE COMPOSITIONS COMPRISING CAFFEINE, METHODS OF USE AND AN APPARATUS FOR USING THE SAME," and filed Jul. 9, 2014, which claims priority to and the benefit of U.S. Provisional Patent Application No. 61/844,772, titled "INHALABLE COMPOSITIONS COMPRISING CAFFEINE, METHODS OF USE AND AN APPARATUS FOR USING THE SAME," and filed on Jul. 10, 2013, the contents all of which are hereby incorporated herein by reference in its entirety for all purposes.

FIELD

The present technology generally relates to compositions, methods and an apparatus relating to the pulmonary delivery of an inhalable composition comprising caffeine.

BACKGROUND

The following background is provided to assist the understanding of the reader. None of the information provided or references cited is admitted to be prior art to the present invention.

Caffeine is a bitter substance that acts on many humans as a central nervous system stimulant, temporarily warding off drowsiness and restoring alertness. It is the most widely used of all psychoactive drugs. Caffeine consumption from all sources has been estimated at around 70 to 76 mg/person/day worldwide and about 210 to 238 mg/day in the US and Canada. In North America, 90% of adults consume caffeine daily. Daily caffeine consumption may reach a value of 2.4 to 4.0 mg/kg (170-300 mg) in a 60- to 70-kg individual, largely from coffee, tea, soft drinks, energy drinks, and chocolate foods. A cup of coffee, a soft drink or an energy drink can have about 80-200 mg, 30-60 mg or 60-280 mg caffeine per serving, respectively.

Caffeine is a hydrophobic compound with relatively low solubility in water. The absorption of caffeine by the oral route, from the gastrointestinal tract, is rapid and reaches 99% in humans in about 45 minutes after ingestion. However, the oral route has disadvantages. The consumption of caffeine via soft drinks, energy drinks and chocolate foods contributes to weight gain and obesity. The consumption of caffeine from coffee and tea contributes to stomach aches and gastrointestinal disorders. Withdrawal symptoms after the discontinuation of caffeine from one's diet may include headache, irritability, inability to concentrate, drowsiness, insomnia, and pain in the stomach.

Therefore, improved formulations of caffeine are needed. Also needed is an efficient means to administer caffeine more directly into the blood steam, relative to the oral route and without the concomitant consumption of foods and beverages that contain caffeine. For example, it would be desirable to provide improved methods and compositions for the pulmonary delivery of caffeine. Although caffeinated powders have been developed for inhalation, these powders are ineffective because they settle on the tongue, mouth and throat of a subject where they are substantially rinsed into the stomach for oral delivery.

Personal electronic vaporizers such as electronic cigarettes have been developed for the pulmonary administration of relatively small concentrations of active compounds. Electronic cigarettes, which generally include a battery, vaporizer (i.e., atomizer), chamber to store the liquid and a mouthpiece, have been used to effectively vaporize actives such as nicotine for pulmonary administration. The quantity of nicotine delivered by electronic cigarettes ranges from "low" doses of about 6-8 µg to "ultra high" doses of about 36-48 µg.

SUMMARY

Described herein are improved compositions, methods and an apparatus relating to the pulmonary delivery of an inhalable composition comprising caffeine, or a salt thereof, and a solvent selected from the group consisting of propylene glycol, glycerol, ethanol, and a combination thereof. Inhalable compositions have been developed that maintain caffeine, or a salt thereof, in aqueous solution and allow such aqueous solutions of caffeine to be heated and vaporized by an apparatus, such as a personal electronic vaporizer or an electronic cigarette, for pulmonary administration to a subject. Following inhalation of the caffeine by the subject, systemic absorption occurs through the thin layer of epithelial cells in the alveolar regions of the lung. Such pulmonary delivery of caffeine may provide more rapid systemic availability than does the oral route and avoids stomach irritation and the need to consume foods or beverages that contain caffeine.

In one aspect, an inhalable composition is provided, comprising caffeine, or a salt thereof, and a solvent selected from the group consisting of propylene glycol, glycerol, ethanol, and a combination thereof. In one embodiment, the inhalable composition further comprises water. Applicants have developed inhalable compositions having suitable ratios of propylene glycol, ethanol and glycerol that retain the caffeine in solution, such as an aqueous solution, and allow it to be efficiently vaporized. Applicants have further developed such inhalable compositions having additional additives, some of which further improve the overall solubility of caffeine. For example, in one non-limiting embodiment, the inhalable composition comprises: about 1 wt. % to about 10 wt % caffeine HCl, about 1 wt. % to about 10 wt % yerba mate leaf extract, about $1 \times 10^{-10}$ wt. % to about $1 \times 10^{-5}$ wt % huperizine, about 1 wt. % to about 30 wt % taurine, about 1 wt. % to about 30 wt % inositol, about 0.1 wt. % to about 3 wt % niacinamide, about 1 wt. % to about 30 wt % phenylalanine, about 1 wt. % to about 30 wt % citicoline, about 1 wt. % to about 30 wt % propylene glycol, about 1 wt. % to about 30 wt % glycerol and water.

In one aspect, an apparatus is provided for the pulmonary administration of an inhalable composition to a subject, wherein: the apparatus is a personal electronic vaporizer; the inhalable composition comprises caffeine, or a salt thereof, and a water-miscible solvent selected from the group consisting of propylene glycol, glycerol, ethanol and a combination thereof; and the apparatus comprises a means to store the inhalable composition as a liquid, a means to heat and transform the liquid into a vapor and a means to administer at least 0.0001 mg caffeine, or a salt thereof, from the vapor to the subject per inhalation by the subject from the apparatus. In one embodiment, the apparatus comprises the inhalable composition.

In yet another aspect, a method is provided for administering an inhalable composition to a subject in need thereof, the method comprising providing the subject with the inhalable composition comprising caffeine, or a salt thereof, and a solvent selected from the group consisting of propylene glycol, glycerol, ethanol and a combination thereof; and an apparatus for the pulmonary administration of the inhalable composition; wherein the method results in a pulmonary administration of at least 0.0001 mg of caffeine from the inhalable composition to the subject.

DETAILED DESCRIPTION

Figure 1:
FIG. 1 is a top exterior view of an exemplary apparatus described herein, according to one illustrative implementation.

In the following detailed description, reference is made to the accompanying drawings, which form a part thereof. The illustrative embodiments described in the detailed description, drawings and claims are not meant to be limiting. Other embodiments may be utilized, and other changes may be made, without departing from the spirit or scope of the subject matter presented here. The present technology is also illustrated by the examples herein, which should not be construed as limiting in any way.

As used herein, the term "pulmonary delivery" means that the mode of delivery targets the lungs of a subject as a means to enter the blood stream of the subject. Generally, not all of a given dosage that is administered by pulmonary delivery reaches both the lungs and the blood stream of the subject. Rather, just a fraction of the dosage that is administered by pulmonary delivery reaches both the lungs and the blood stream of the subject.

As used herein, the terms "glycerol," "glycerin," "vegetable glycerin" and "vegetable glycerol" are used interchangeably.

As used herein, the term "vapor" is used to describe a droplet of liquid that is substantially free (e.g., at least 80-99% free) of solids.

As used herein, the term "water-miscible solvent" is meant to include all solvents other than water that dissolve with water at a 1:1 ratio at 25° C.

As used herein, the terms "personal electronic vaporizer" and "vaporizer" are meant to include all such devices, including and resembling electronic cigarettes that are known to those of ordinary skill in the art in addition to the personal electronic vaporizer apparatus that is disclosed herein. Non-limiting representative electronic cigarettes are described in the published patent applications US 2012/0273589 and US 2012/0279512, both to Lik Hon.

As used herein, "active ingredient" refers to a compound that provides a pharmacological activity. By way of example, but not by way of limitation, in some embodiments, active ingredients include, but are not limited to, caffeine, *panax ginseng*, gingko biloba, bitter orange, colanut, guarana, natrum carbonicum, green tea, cocoa extract, and yerba mate.

As used herein, "inactive ingredient" refers to an inert compound or substance. In some embodiments, an inactive ingredient serves as a diluent or vehicle for the compound. By way of example, but not by way of limitation, in some embodiments, inactive ingredients include, but are not limited to, USP Kosher propylene glycol, USP Kosher vegetable glycerin, P57 Hoodia, ethanol, water, natural flavoring, inositol, and N-acetyl L tyrosine.

A. INHALABLE COMPOSITIONS

Described herein, in one aspect, are inhalable compositions comprising caffeine, or a salt thereof, and one or more water-miscible solvents, wherein the one or more water-miscible solvents each has a boiling point greater than 150° C. In one embodiment, the water-miscible solvent is selected from the group consisting of propylene glycol, glycerol, ethanol and a combination thereof. These inhalable compositions are formulated for pulmonary delivery to a subject. Specifically, the inhalable compositions are formulated for vaporization by an apparatus, such as a personal electronic vaporizer or electronic cigarette that stores the inhalable composition as a liquid, heats the inhalable composition into a vapor phase and delivers the inhalable composition to the subject as a vapor via inhalation.

It is contemplated that, because lung tissue is sensitive to absorption, the stimulating effects of caffeine will be felt by a subject sooner (e.g., 1-10 minutes) upon inhalation relative to the longer periods (e.g., 30-45 minutes) required for caffeine to take effect upon ingestion. Upon pulmonary administration, caffeine bypasses acid and bile in the stomach, and is expected to reach the central nervous system sooner than the oral route. It is contemplated that the inhalable compositions described herein will not cause stomach aches that can occur following the consumption of coffee or tea.

As noted, the inhalable compositions described herein include caffeine, or a salt thereof, and a water-miscible solvent, particularly those selected from the group consisting of propylene glycol, glycerol, ethanol and a combination thereof. Propylene glycol, having a boiling point of 188.2° C. and glycerol having a boiling point of 290° C., act as solvents and as thickening agents. Propylene glycol, glycerol and ethanol also provide a relatively even heating of the inhalable composition as it is vaporized by the apparatus. Further, propylene glycol, glycerol and ethanol provide tangible plumes of vapor that retain the caffeine within the vapor droplets.

The quantity of propylene glycol that is added to the inhalable compositions described herein can and will vary. In some embodiments the inhalable compositions described herein comprise 0 wt. %, 1 wt. %, 2 wt. %, 3 wt. %, 4 wt. %, 5 wt. %, 6 wt. %, 7 wt. %, 8 wt. %, 9 wt. %, 9.5 wt. %, 10 wt. %, 10.5 wt. %, 11 wt. %, 12 wt. %, 13 wt. %, 14 wt. %, 15 wt. %, 16 wt. %, 17 wt. %, 18 wt. %, 19 wt. %, 20 wt. %, 30 wt. %, 40 wt. %, 50 wt. % or a percentage between any two of these values of propylene glycol relative to the of the entire inhalable composition comprising caffeine. In some embodiments, the inhalable composition comprises propylene glycol and does not contain glycerol.

The quantity of glycerol that is added to the inhalable compositions described herein can and will vary. In some embodiments the inhalable compositions described herein comprise 0 wt. %, 1 wt. %, 2 wt. %, 3 wt. %, 4 wt. %, 5 wt. %, 6 wt. %, 7 wt. %, 8 wt. %, 9 wt. %, 9.5 wt. %, 10 wt. %, 10.5 wt. %, 11 wt. %, 12 wt. %, 13 wt. %, 14 wt. %, 15 wt. %, 16 wt. %, 17 wt. %, 18 wt. %, 19 wt. %, 20 wt. %, 30 wt. %, 40 wt. %, 50 wt. % or a percentage between any two of these values of glycerol relative to the of the entire inhalable composition comprising caffeine. In some embodiments, the inhalable composition comprises glycerol and does not contain propylene glycol.

The quantity of ethanol that is added to the inhalable compositions described herein can and will vary. In some embodiments the inhalable compositions described herein comprise 0 wt. %, 1 wt. %, 2 wt. %, 3 wt. %, 4 wt. %, 5 wt. %, 6 wt. %, 7 wt. %, 8 wt. %, 9 wt. %, 9.5 wt. %, 10 wt. %, 10.5 wt. %, 11 wt. %, 12 wt. %, 13 wt. %, 14 wt. %, 15 wt. %, 16 wt. %, 17 wt. %, 18 wt. %, 19 wt. %, 20 wt. %, 30 wt. %, 40 wt. %, 50 wt. % or a percentage between any two of these values of ethanol relative to the of the entire inhalable composition comprising caffeine. In some embodiments, the inhalable composition comprises ethanol and does not contain glycerol or propylene glycol.

In some embodiments, the inhalable composition described herein comprises propylene glycol and glycerol, each in any of the wt % amounts described herein, such that the inhalable composition has a wt/wt % ratio of propylene glycol to glycerol (i.e., propylene glycol:glycerol) of 1:1,000, 1:500, 1:100, 1:50, 1:25, 1:20, 1:15, 1:10, 1:5, 1:4, 1:3, 1:2, 1.1.5, 1:1.4, 1:1.3, 1:1.2, 1:1.1, 1:1, 1.1:1, 1.2:1, 1.3:1, 1.4:1, 1.5:1, 2:1, 3:1, 4:1, 5:1, 10:1, 15:1, 20:1, 25:1, 50:1, 100:1, 1,000:1 or a ration between any two of these values. In some embodiments, the inhalable composition comprises propylene glycol and glycerol, and the inhalable composition has a ratio of propylene glycol to glycerol of about 2:1 to about 1:2.

In some embodiments, the inhalable composition described herein comprises propylene glycol and ethanol, each in any of the wt % amounts described herein, such that the inhalable composition has a wt/wt % ratio of propylene glycol to ethanol (i.e., propylene glycol:ethanol) of 1:1,000, 1:500, 1:100, 1:50, 1:25, 1:20, 1:15, 1:10, 1:5, 1:4, 1:3, 1:2, 1.1.5, 1:1.4, 1:1.3, 1:1.2, 1:1.1, 1:1, 1.1:1, 1.2:1, 1.3:1, 1.4:1, 1.5:1, 2:1, 3:1, 4:1, 5:1, 10:1, 15:1, 20:1, 25:1, 50:1, 100:1, 1,000:1 or a ration between any two of these values. In some embodiments, the inhalable composition comprises propylene glycol and ethanol, and the inhalable composition has a ratio of propylene glycol to ethanol of about 2:1 to about 1:2.

In some embodiments, the inhalable composition described herein comprises ethanol and glycerol, each in any of the wt % amounts described herein, such that the inhalable composition has a wt/wt % ratio of ethanol to glycerol (i.e., ethanol:glycerol) of 1:1,000, 1:500, 1:100, 1:50, 1:25, 1:20, 1:15, 1:10, 1:5, 1:4, 1:3, 1:2, 1.1.5, 1:1.4, 1:1.3, 1:1.2, 1:1.1, 1:1, 1.1:1, 1.2:1, 1.3:1, 1.4:1, 1.5:1, 2:1, 3:1, 4:1, 5:1, 10:1, 15:1, 20:1, 25:1, 50:1, 100:1, 1,000:1 or a ration between any two of these values. In some embodiments, the inhalable composition comprises ethanol and glycerol, and the inhalable composition has a ratio of ethanol to glycerol of about 2:1 to about 1:2.

In some embodiments, the inhalable composition described herein comprises propylene glycol, ethanol, and glycerol, each in any of the wt % amounts described herein.

In any of the embodiments described herein, the inhalable composition further comprises water. In some embodiments the inhalable composition described herein comprises 0 wt. %, 1 wt. %, 2 wt. %, 3 wt. %, 4 wt. %, 5 wt. %, 6 wt. %, 7 wt. %, 8 wt. %, 9 wt. %, 9.5 wt. %, 10 wt. %, 10.5 wt. %, 11 wt. %, 12 wt. %, 13 wt. %, 14 wt. %, 15 wt. %, 16 wt.

%, 17 wt. %, 18 wt. %, 19 wt. %, 20 wt. %, 30 wt. %, 40 wt. %, 50 wt. %, 60 wt. %, 70 wt. %, 80 wt. %, 90 wt. %, or a percentage between any two of these values of water relative to the of the entire inhalable composition comprising caffeine.

In some embodiments, the inhalable composition described herein is a vapor comprising liquid droplets. The liquid droplets have an average diameter that facilitates administration of the caffeine within the droplets to the subject via the pulmonary route. For example, the liquid droplets may have an average diameter of about 1, 2, 3, 4, 5, 6, 7, 8, 9, 10, 11, 12, 13, 14, 15, 16, 17, 18, 19, 20 microns, or an average diameter between any two of these values.

In some embodiments, the inhalable compositions described herein further comprise suitable additives. For example, in some embodiments, the inhalable composition further comprises one or more additives such as yerba mate leaf extract, huperizine, taurine, inositol, niacinamide, phenylalanine, citicoline, or a salt of any thereof.

Yerba Mate extract is the product of yerba mate plant brewed or distilled so that caffeine (or maffeine) is left in the residue. The absorption rate of maffeine through the body is slower than that of caffeine and may produce a more uplifting feeling than caffeine. Huperzine A may cause an increase in the levels of acetylcholine in a subject. Huperzine A may also offset the negative jitteriness that caffeine may cause in a subject. Taurine has been found to help dissolve the caffeine in the inhalable compositions described herein and may also help to facilitate the absorption of caffeine into the blood. Taurine may also minimize the caffeine crash that occurs in some patients following administration of caffeine. Taurine may also serve as a relaxant to offset the jitteriness caused by caffeine and help a subject go to sleep. Inositol is a flavorant that improves the taste of inhalable compositions comprising caffeine. Specifically, it reduces the bitterness of caffeine. Inositol has also been found improve the solubility of caffeine in the inhalable compositions described herein. Niacinamide, also known as vitamin B-3, plays important roles in the energy production process in cells. Niacinamide boosts the effects of caffeine to create longer lasting stimulation in a subject. Niacinamide may also help reduce the "short of breath" feeling that some people complain of after ingesting caffeine. Phenylalanine may reduce caffeine headache associated with caffeine and may also help with caffeine withdrawal. Citicoline may play a role in neurotransmission and might help support brain function.

Other suitable additives include, but are not limited to, N-Acetyl L Tyrosine, *Panax Ginseng* (*Aralia quinquefolia*), Gingko Biloba (*Ginkgo biloba* L.), Bitter Orange (*Citrus aurantium* L.), Cola-Nut (*Cola acuminate*), Guarana (*Paullinia cupana*), Natrum Carbonicum, Green Tea (*Camellia sinensis*), Cocoa Extract (*Theobroma cacao* L.), Licorice (*Glycyrrhiza glabra* L.), Natrum Carbonicum, Ginger (*Zingiber officinale* Rosc.), P57 Hoodia, Glucuronolactone, Yerba Mate (*Ilex paraguensis* St. Hil.), *Garcinia Cambogia*, Hoodia *Gordonii*, Kelp, and Peppermint (Mentholum). In some embodiments, the additional additives are useful for energy and/or diet support. In some embodiments, the additional additives are natural flavoring.

In one non-limiting embodiment, the inhalable composition comprises about 1 wt. % to about 10 wt % caffeine HCl, about 1 wt. % to about 10 wt % yerba mate leaf extract, about $1 \times 10^{-10}$ wt. % to about $1 \times 10^{-5}$ wt % huperizine, about 1 wt. % to about 30 wt % taurine, about 1 wt. % to about 30 wt % inositol, about 0.1 wt. % to about 3 wt % niacinamide, about 1 wt. % to about 30 wt % phenylalanine, about 1 wt.

% to about 30 wt % citicoline, about 1 wt. % to about 30 wt % propylene glycol, about 1 wt. % to about 30 wt % glycerol, and water.

In another embodiment, the inhalable composition comprises about 1-5 wt % caffeine HCl, about 1-5 wt % yerba mate leaf extract, about $1\times10^{-9}$ to $1\times10^{-6}$ wt % huperizine, about 1-15 wt % taurine, about 1-15 wt % inositol, about 0.1-2.0 wt % niacinamide, about 1-15 wt % phenylalanine, about 1-15 wt % citicoline, about 1-15 wt % propylene glycol, about 1-15 wt % glycerol, and water. In some embodiments, the water is de-ionized water.

In another embodiment, the inhalable composition comprises about 3.8 wt % caffeine HCl, about 2.5 wt % yerba mate leaf extract, about $1\times10^{-8}$ wt % huperizine, about 9.5 wt % taurine, about 9.5 wt % inositol, about 0.6 wt % niacinamide, about 9.5 wt % phenylalanine, about 7.6 wt % citicoline, about 9.5 wt % propylene glycol, about 9.5 wt % glycerol, and water. In some embodiments, the water is de-ionized water.

In one embodiment, the inhalable composition further comprises about 1 wt %, 5 wt %, 10 wt %, 15 wt %, 20 wt %, 25 wt %, 30 wt %, or a range between any two of these values, of a flavorant. For example, the flavorant may be selected from the group consisting of citric acid, lemon extract, lime extract, orange extract, peppermint, spearmint, cinnamon and a combination thereof.

In any of the embodiments described herein, the inhalable composition further comprises nicotine. In some embodiments the inhalable composition described herein comprises 0 wt. %, 0.1 wt. %, 0.2 wt. %, 0.3 wt. %, 0.4 wt. %, 0.5 wt. %, 1 wt. %, 2 wt. %, 5 wt. %, or a percentage between any two of these values of nicotine relative to the of the entire inhalable composition comprising caffeine.

In certain embodiments, the inhalable compositions and formulations described herein are for the pulmonary administered to a subject (e.g., a human) and may contain one or more pharmaceutically-acceptable excipients, or carriers. Suitable excipients and their formulations are described in Remington's Pharmaceutical Sciences, 16th ed., 1980, Mack Publishing Co., edited by Oslo et al. Typically, an appropriate amount of a pharmaceutically-acceptable salt is used in the formulation to render the formulation isotonic. Examples of the pharmaceutically-acceptable excipients include liquids such as saline, Ringer's solution and dextrose solution.

The pH of the formulation can be set at any desired level which is not damaging to lung surfaces. Although it is desirable to have a low pH formulation (acidic) to avoid interaction with certain types of plastic containers it is generally more desirable to have a high pH formulation (basic) to increase the absorption of the caffeine from the lung into the circulatory system. The pH of the inhalable compositions described herein is generally from about 3 to about 8, or from about 3 to about 7, although the pH may be varied. The inhalable composition or formulation may also comprise a lyophilized powder or other optional excipients suitable to the present inhalable composition or formulation including sustained release preparations known to those of skill in the art.

Other suitable excipients can be added to the inhalable compositions described herein. For example, the inhalable compositions or formulations described herein for inhalation can include, e.g., one or more surfactants to aid in solubility and stability of formulation constituents. Surfactants can be present in formulations of the invention in a concentration ranging from about 0.001 weight percent to about 2 weight percent, or about 0.01 weight percent to about 1 weight percent. The surfactants can include, e.g., nonionic detergents, such as polyethylene glycol sorbitan monolaurate (Tween 20), polyoxyethylenesorbitan monooleate (Tween 80), block copolymers of polyethylene and polypropylene glycol (Pluronic), non-ionic surfactants, ionic surfactants and/or the like.

Examples of suitable non-ionic surfactants are alkylphenyl alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone oils, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers and mixtures of these, polyacrylates and acrylic acid graft copolymers. Other nonionic surfactants are known per se to those skilled in the art and have been described in the literature. Preferred substances are polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers and mixtures of these. Particularly preferred surfactants include polymers of a mixture of polyoxyethylene and polyoxypropylene such as Pluronic F68 (available from BASF).

Examples of suitable ionic surfactants are alkylarylsulfonates, phenylsulfonates, alkyl sulfates, alkyl sulfonates, alkyl ether sulfates, alkyl aryl ether sulfates, alkyl polyglycol ether phosphates, polyaryl phenyl ether phosphates, alkylsulfosuccinates, olefin sulfonates, paraffin sulfonates, petroleumsulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol and, if appropriate, urea, lignin-sulfite waste liquor, including their alkali metal, alkaline earth metal, ammonium and amine salts, alkyl phosphates, quaternary ammonium compounds, amine oxides, betaines, and mixtures of these. Preferred substances include Pluronic F68 or Pluronic F188 with polyoxyethylene sorbitan monolaurate (e.g., Tween 20, available from Sigma) being particularly preferred.

The inhalable compositions and formulations described herein may include one or more buffers. Buffers can be present, e.g., to control pH, enhance stability, affect constituent solubility, provide comfort on administration, and the like. Formulation pH can be controlled in the range from about pH 3 to about pH 10, from about pH 6 to about pH 8, from about pH 7 to about pH 7.4, or about pH 7.2. Preferred buffers are often paired acid and salt forms of a buffer anion generally recognized as safe for the particular route of administration of the bioactive material. Typical buffers for use in the formulations and inhalable compositions of the invention include, e.g., potassium phosphate, sodium phosphate, sodium acetate, histidine, imidazole, sodium citrate, sodium succinate, ammonium bicarbonate, carbonates, and the like. Generally, buffers are used at molarities from about 1 mM to about 2 M, with from about 2 mM to about 1 M being preferred, and from about 10 mM to about 0.5 M being especially preferred, and 25 mM to 50 mM being particularly preferred.

Because the inhalable compositions described herein comprises propylene glycol, glycerol, ethanol, or a combination thereof they are generally more viscous than water. In one embodiment, any of the inhalable compositions described herein has a viscosity at 20° C. of about 0.001 Pa·s, about 0.01 Pa·s, about 0.1 Pa·s, about 1.0 Pa·s, about 1.5 Pa·s, or a viscosity between any two of the these values.

The inhalable compositions described herein are formulated to provide at least 0.0001 mg of caffeine to a subject per inhalation of any one of these compositions. For example, the inhalable compositions described herein may be formulated to provide at least about 0.0001, 0.001, 0.01, 0.1, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 100, 105, 110, 125, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 mg, or an amount between any two of these values, of caffeine or a salt thereof, to the subject per inhalation (i.e., vape). Thus, in some embodiments, the composition is formulated to provide about 0.0001 mg to about 10 mg of caffeine or a salt thereof to the subject per inhalation by the subject. In some embodiments, the composition is formulated to provide about 10 mg to about 20 mg of caffeine or a salt thereof to the subject per inhalation by the subject. In some embodiments, the composition is formulated to provide about 20 mg to about 30 mg of caffeine or a salt thereof to the subject per inhalation by the subject. In some embodiments, the composition is formulated to provide about 30 mg to about 40 mg of caffeine or a salt thereof to the subject per inhalation by the subject. In some embodiments, the composition is formulated to provide about 40 mg to about 50 mg of caffeine or a salt thereof to the subject per inhalation by the subject. In some embodiments, the composition is formulated to provide about 50 mg to about 60 mg of caffeine or a salt thereof to the subject per inhalation by the subject. In some embodiments, the composition is formulated to provide about 60 mg to about 70 mg of caffeine or a salt thereof to the subject per inhalation by the subject. In some embodiments, the composition is formulated to provide about 70 mg to about 80 mg of caffeine or a salt thereof to the subject per inhalation by the subject. In some embodiments, the composition is formulated to provide about 80 mg to about 90 mg of caffeine or a salt thereof to the subject per inhalation by the subject. In some embodiments, the composition is formulated to provide about 90 mg to about 100 mg of caffeine or a salt thereof to the subject per inhalation by the subject. In some embodiments, the composition is formulated to provide about 100 mg to about 110 mg of caffeine or a salt thereof to the subject per inhalation by the subject. In some embodiments, the composition is formulated to provide about 110 mg to about 120 mg of caffeine or a salt thereof to the subject per inhalation by the subject. In some embodiments, the composition is formulated to provide about 120 mg to about 130 mg of caffeine or a salt thereof to the subject per inhalation by the subject. In some embodiments, the composition is formulated to provide about 130 mg to about 140 mg of caffeine or a salt thereof to the subject per inhalation by the subject. In some embodiments, the composition is formulated to provide about 140 mg to about 150 mg of caffeine or a salt thereof to the subject per inhalation by the subject. In some embodiments, the composition is formulated to provide about 150 mg to about 160 mg of caffeine or a salt thereof to the subject per inhalation by the subject. In some embodiments, the composition is formulated to provide about 160 mg to about 170 mg of caffeine or a salt thereof to the subject per inhalation by the subject. In some embodiments, the composition is formulated to provide about 170 mg to about 180 mg of caffeine or a salt thereof to the subject per inhalation by the subject. In some embodiments, the composition is formulated to provide about 180 mg to about 190 mg of caffeine or a salt thereof to the subject per inhalation by the subject. In some embodiments, the composition is formulated to provide about 190 mg to about 200 mg of caffeine or a salt thereof to the subject per inhalation by the subject. In some embodiments, the composition is formulated to provide about 200 mg to about 210 mg of caffeine or a salt thereof to the subject per inhalation by the subject. In some embodiments, the composition is formulated to provide about 210 mg to about 220 mg of caffeine or a salt thereof to the subject per inhalation by the subject. In some embodiments, the composition is formulated to provide about 220 mg to about 230 mg of caffeine or a salt thereof to the subject per inhalation by the subject. In some embodiments, the composition is formulated to provide about 230 mg to about 240 mg of caffeine or a salt thereof to the subject per inhalation by the subject. In some embodiments, the composition is formulated to provide about 240 mg to about 250 mg of caffeine or a salt thereof to the subject per inhalation by the subject. In some embodiments, the composition is formulated to provide about 250 mg to about 260 mg of caffeine or a salt thereof to the subject per inhalation by the subject. In some embodiments, the composition is formulated to provide about 260 mg to about 270 mg of caffeine or a salt thereof to the subject per inhalation by the subject. In some embodiments, the composition is formulated to provide about 270 mg to about 280 mg of caffeine or a salt thereof to the subject per inhalation by the subject. In some embodiments, the composition is formulated to provide about 280 mg to about 290 mg of caffeine or a salt thereof to the subject per inhalation by the subject. In some embodiments, the composition is formulated to provide about 290 mg to about 300 mg of caffeine or a salt thereof to the subject per inhalation by the subject.

The inhalable compositions described herein are formulated to provide less than 1 mg of nicotine to a subject per inhalation of any one of these compositions. For example, the inhalable compositions described herein may be formulated to provide at least about 1, 2, 3, 4, 5, 6, 7, 8, 9, 10, 11, 12, 13, 14, 15, 16, 17, 18, 19, 20, 25, 30, 35, 40, 45 or 50 µg, or an amount between any two of these values, of nicotine or a salt thereof, to the subject per inhalation (i.e., vape).

In another embodiment, the inhalable compositions of the present technology includes one or more active ingredients selected from the group consisting of Caffeine (Caffeinum), *Panax Ginseng* (*Aralia quinquefolia*), Gingko Biloba (*Ginkgo biloba* L.), Bitter Orange (*Citrus aurantium* L.), Cola-Nut (*Cola acuminate*), Guarana (*Paullinia cupana*), Natrum Carbonicum, Green Tea (*Camellia sinensis*), Cocoa Extract (*Theobroma cacao* L.), and Yerba Mate (*Ilex paraguensis* St. Hil.). In some embodiments, the inhalable composition also includes one or more inactive ingredients selected from the group consisting of USP Kosher propylene glycol, USP Kosher vegetable glycerin, ethanol, water, glucuronolactone, natural flavoring, inositol, and N-acetyl L tyrosine. In some embodiments, the inhalable composition provides energy.

In another embodiment, the inhalable compositions of the present technology includes one or more active ingredients selected from the group consisting of Caffeine (Caffeinum), Peppermint (Mentholum), Bitter Orange (*Citrus aurantium* L.), Green Tea (*Camellia sinensis*), Licorice (*Glycyrrhiza glabra* L.), Natrum Carbonicum, Ginger (*Zingiber officinale* Rosc.), *Garcinia Cambogia*, Hoodia *Gordonii*, Kelp, and Yerba Mate (*Ilex paraguensis* St. Hil.). In some embodiments, the inhalable composition also includes one or more inactive ingredients selected from the group consisting of USP Kosher propylene glycol, USP Kosher vegetable glycerin, P57 Hoodia, ethanol, water, natural flavoring, inositol, and N-acetyl L tyrosine. In some embodiments, the inhalable composition provides energy. In some embodiments, the inhalable composition provides diet support.

B. APPARATUS

FIG. 1 is a top view of an exemplary implementation of a vaporizer apparatus 100 (also referred to as a vaporizer 100). The exterior of the vaporizer 100 may include the body section 102 and the mouthpiece 104. As described below, the body 104 of the vaporizer 100 may store the components that are responsible for the function and control of the vaporizer 100. The mouthpiece 104 may house the cartridge used to store the inhalable composition. In general, when a user inhales on the mouthpiece 104, the vaporizer 100 delivers a predetermined amount of the inhalable composition to the user in a vapor form.

Figure 2:
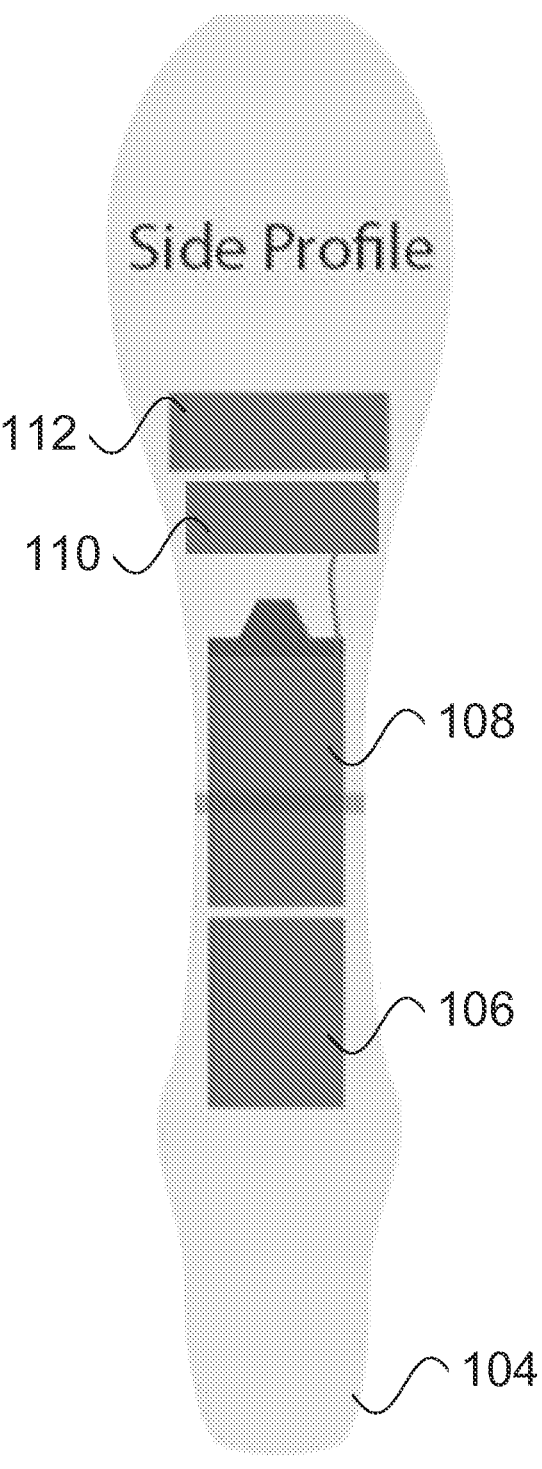
FIG. 2 is an interior view of an exemplary apparatus described herein, according to one illustrative implementation.

FIG. 2 is a side view of the vaporizer 100. FIG. 2 illustrates an exemplary configuration of the layout of components within the vaporizer 100. As a brief overview, the vaporizer 100 may include a cartridge 106, an atomizer 108, a controller 110, and a power supply 112.

Now referring to the components of the vaporizer 100 in greater detail. The cartridge 106 may be configured to house any of the inhalable composition described herein. In some implementations, the inhalable composition includes an additive selected from the group consisting of yerba mate leaf extract, huperizine, taurine, inositol, niacinamide, phenylalanine, citicoline, or a salt of any thereof, and a combination thereof.

The housing of the cartridge 106 may be made from any food grade material. For example, the housing of the cartridge 106 may include polyethylene terephthalate, high density polyethylene, polyvinyl chloride, or any combination thereof. In other implementations, the housing of the cartridge 106 may include metals or allows. In some implementations, the cartridge 106 is configured to allow the inhalable composition to pass to the atomizer 108 in a liquid form and then pass through the mouthpiece 104 to the user in a vapor form. The cartridge 106 may include an air-liquid separator which allows the inhalable composition to exit the mouthpiece 104 in substantially only vapor form and not liquid form. In some implementations, the air-liquid separator is a sponge or membrane.

In some implementations, the cartridge 106 is refillable and in some implementations the cartridge 106 is disposed of once the inhalable composition is consumed. The cartridge 106 may be a component of, or coupled to the mouthpiece 104, such that the mouthpiece 104 section may be replaced when replacing the cartridge 106. In some implementations, the mouthpiece 104 and/or the body 102 (and components housed within the body 102) of the vaporizer 100 may be reusable. For example, once the inhalable composition within the cartridge 106 has been consumed, a user may replace the cartridge 106 and continue using the vaporizer 100. In other implementations, the vaporizer 100 may be disposed of after the inhalable composition in the cartridge 106 is consumed.

In some implementations, the cartridge 106 may be configured to store an inhalable composition that includes between about 0.0001 mg and about 10 mg, between about 0.001 mg and about 5 mg, between about 0.01 mg and about 2.5 mg, or between about 0.1 mg and 1.0 mg of caffeine in solution. In some implementation, the cartridge 106 may be configured to store an inhalable composition that includes between about 10 mg and about 200 mg, between about 30 mg and about 180 mg, between about 50 mg and about 160 mg, between about 70 mg and about 140 mg, between about 90 mg and about 120 mg, or between about 100 mg and about 110 mg of caffeine in solution. In some embodiments, the cartridge 106 may be configured to store an inhalable composition that includes between about 200 mg and about 2000 mg, between about 400 mg and about 1800 mg, between about 600 mg and about 1600 mg, between about 800 mg and about 1400 mg, or between about 1000 mg and about 1200 mg of caffeine in solution.

The cartridge 106 may be coupled to the atomizer 108 such that between about 0.0001 mg and about 5 mg, between about 5 mg and 15 mg, between about 15 mg and 25 mg, between about 25 mg and 30 mg, between about 30 mg and 35 mg, between about 35 mg and 40 mg, between about 40 mg and 45 mg, between about 45 mg and 50 mg, between about 50 mg and 55 mg, between about 55 mg and 60 mg, between about 60 mg and 65 mg, between about 65 mg and 70 mg, between about 70 mg and 85 mg, between about 85 mg and 90 mg, between about 90 mg and 95 mg, between about 95 mg and 100 mg, between about 100 mg and 105 mg, between about 105 mg and 110 mg, between about 110 mg and 120 mg, between about 120 mg and 130 mg, between about 130 mg and 140 mg, between about 140 mg and 150 mg, between about 150 mg and 160 mg, between about 160 mg and 170 mg, between about 170 mg and 180 mg, between about 180 mg and 190 mg, between about 190 mg and 200 mg, between about 200 mg and 210 mg, between about 210 mg and 220 mg, between about 220 mg and 230 mg, between about 230 mg and 240 mg, between about 240 mg and 250 mg, between about 250 mg and 260 mg, between about 260 mg and 270 mg, between about 270 mg and 280 mg, between 280 mg and 290 mg, or between 290 mg and 300 mg of caffeine is delivered to the atomizer 108 during each inhalation cycle of the device. In some implementations, the coupling between the cartridge 106 and the atomizer 108 may include a fluid flow channel. In some implementations, the inhalable composition may be drawn into the atomizer 108 through capillary action. For example, a wicking metal, such as silica, may draw the liquid inhalable composition from the cartridge 106 to the atomizer 108.

Once the inhalable composition is received by the atomizer 108, the atomizer 108 vaporizes the inhalable composition. In some implementations, the atomizer 108 may include a heating element that heats and vaporizes the inhalable composition. The atomizer 108 may heat the inhalable compositions comprising caffeine, or a salt thereof, and a solvent selected from the group consisting of propylene glycol, glycerol, ethanol and a combination thereof, to form a vapor. In some embodiments, the atomizer 108 heats the inhalable composition into a vapor at about 250° F., 300° F., 350° F., 400° F., 450° F., 500° F., 550° F., or a temperature between any two of these values. In one embodiment, the vaporizer 100 is an electronic cigarette. The vaporized inhalable composition may be referred to as a vapor and may include liquid droplets of caffeine, which may be inhaled by the user.

The size distribution of the diameter of the vapor droplets that are delivered by the apparatus is important to the therapeutic efficacy of the caffeine within the inhalable composition when delivered by inhalation. Liquid droplets of greater than about 20 micrometers in mean aerodynamic diameter generally achieve reduced entry into the lungs and are captured in the nasal-pharyngeal passages. Thus, the caffeine compositions for inhalation, as described herein, to be delivered via pulmonary administration, are generally formulated so that the median aerodynamic diameter of the vapor droplets is below about 10 micrometers. The size distribution of the diameter of the vapor droplets is within a size range of about between about 0.5, 1, 2.5, 10, 20 microns in diameter. The smaller droplet sizes, on the order of 0.5 to 2.5 micrometers, are prepared for delivery of caffeine to the alveolar sacs deep in the lungs. Droplet size may be selected to stimulate either the upper respiratory tract or the lower respiratory tract or both. Further, the vapor and each inhalation thereof may contain caffeine in an amount of about 0.0001 mg to about 20.0 mg per inhalation.

In one implementation, the vaporizer 100 includes a porous membrane. As indicated above the rate and amount of caffeine that can be absorbed can be varied by changing the constituent (e.g., caffeine, propylene glycol, glycerol and/or ethanol) concentration of and/or pH of the caffeine inhalable composition in the packets. However, it is also possible to decrease the amount of caffeine actually delivered to the patient's circulatory system by changing the size of the pores in the membrane. When the pore size is in a preferred range then a relatively high amount of the formulation, when aerosolized, will reach the subject's deep lungs and rapidly move from the lungs into the subject's circulatory system. However, by making the pores larger the aerosolized droplets created also become larger. The larger droplets will not move into the deep lungs as efficiently as the smaller droplets. For example, with oral inhalation at high to moderate inspiratory flow rates, a significant number of droplets with aerodynamic size greater than 5 micron would deposit in the oropharynx from where they are not rapidly absorbed into the subject's circulatory system.

Although the vaporizer 100 described herein can be configured to target certain areas of the respiratory tract with the inhalable compositions described herein, it will be understood by those skilled in the art that it will not be possible to provide an apparatus which exclusively administers droplets only to a particular area of a respiratory tract. In general, smaller size droplets will deposit in the lung more deeply as compared to larger size droplets. Further, it is generally not desirable to make the droplets smaller than 0.5 microns. When the droplets are sufficiently small, they can be inhaled and exhaled back out without being deposited at all, unless the subject holds their breath for sufficient length of time, typically several seconds, for those droplets to deposit. Further, it is generally not desirable to make the droplets larger than 20 microns because droplets which are larger than this size generally deposit very high up in the respiratory tract and as such do not reach the blood quickly. When referring to targeting an area of the respiratory tract those skilled in the art will understand that it is matter of probabilities of deposition and that those probabilities can vary based on the size of the droplets. It is also understood by those skilled in the art that vaporized droplets often do not have a stable size. For example, droplets can pick up moisture from the air in the respiratory tract and grow in size. Volatile components of droplets can evaporate and make the droplet size smaller. These changes may also cause changes in the density of the droplets that affects their aerodynamic size.

Referring again to the vaporizer 100, the atomizer 108 may be coupled to the controller 110 and/or the power supply 112. In some implementations, the controller 110 may include a microprocessor. The controller 110 may also include computer readable media on which processor executable instructions are stored. When executed by the microprocessor, the instructions may cause the microprocessor heat the atomizer 108 to one of the above described predetermined temperatures in order to vaporize the inhalable composition. Additionally, and as described further below, the controller 110 may also regulate the amount of caffeine that a user may ingest.

The controller 110 may control the activation of the atomizer 108, and thus the dosage of caffeine that is delivered to a user. For example, the controller 110 may include a flow sensor, which may detect the inhalation of a user and activate the atomizer 108. In other implementations, the controller 110 may activate the atomizer 108 when the user activates a button or other switch located on the vaporizer 100. In some implementations, the controller 110 allows the user to select what temperature the atomizer 108 heats the liquid inhalable composition.

When executed the processor executable instructions may cause the controller 110 to limit or control the amount of caffeine and/or inhalable composition a user may ingest. In one embodiment, the controller 112 provides a delay of about 4 to 10 seconds between inhalations (i.e., vapes). The delay may promote the safety of the user. In some implementations, the user may require from about 1 to about 40 vapes to administer an effective dose of caffeine equivalent to that found in a cup of coffee (e.g., about 200 mg of caffeine).

As noted, the controller may allow the vaporizer 100 to administer at least 0.0001 mg caffeine, or a salt thereof, such as about 2 mg to about 50 mg, from the vaporizer 100 to the user per inhalation by the user. As such, the vaporizer 100 described herein can be used to administer one or more inhalations to a user to achieve an effective dose of approximately 20, 40, 60, 80, 100, 200 mg or more of caffeine to a subject over the course of one or more inhalations from the vaporizer 100 by the user.

In some implementations, the controller 110 may cause the vaporizer 100 to enter a refractory state for a predetermined amount of time after the administration of one or more vapes. During the refractory period, the controller 110 may not allow the vaporizer 100 to administer additional vapes to the user. For example, after a user draws two inhalations, the controller 110 may not allow another inhalation to be drawn from the vaporizer 100 for 4 hours. The predetermined amount of time may be between about 15 minutes and about 30 minutes, between about 30 minutes and about 1 hour, between about 1 hour and about 4 hours, between about 4 hours and about 8 hours, and between about 8 hours and about 24 hours.

In a similar implementation, the controller 110 may limit the number of vapes (or caffeine) that may be administered within a predetermined time window. In these implementations, the vaporizer 100 may not enter a refractory state until a predetermined number of vapes have been administered. For example, the controller 110 may allow the user to draw 10 vapes over the course of one hour. In some implementations, the predetermined amount of time may be between about 15 minutes and about 30 minutes, between about 30 minutes and about 1 hour, between about 1 hour and about 4 hours, between about 4 hours and about 8 hours, and between about 8 hours and about 24 hours.

In general, the above described control sequences, or similar control sequences, may be used to limit the amount of caffeine that a user is allowed to consume via the vaporizer 100. The controller 110 may control the inter-vape timing, the amount of caffeine per vape, and the amount of caffeine in a dosage cycle (i.e., the amount of caffeine that a user is allowed to ingest over a given predetermined time window). The controller 110 may limit the amount of caffeine in a dosage cycle to between about 0.0001 mg and about 5 mg, between about 5 mg and about 15 mg, between about 15 mg and about 50 mg, between about 50 mg and about 100 mg, between about 100 mg and about 500 mg of caffeine, and, as described above, the predetermined amount of time may range from 15 minutes to 24 hours.

In some implementations, controller 110 may include analog circuitry and the control methods described herein may implemented with analog logic and/or digital logic.

The vaporizer 100 is powered by a power supply 112. In some implementations, the power supply 112 is a battery. The battery may be a rechargeable battery, such as a lithium ion battery. In some implementations, the battery may be recharged without removing the battery from the vaporizer 100. In other implementations, the power supply 112 may be a non-rechargeable battery. In yet other implementations, the power supply 112 may include an AC (alternating current) adapter that allows the vaporizer 100 to be powered by alternating current (e.g., power from a wall outlet). The power supply 112 may provide between about 3 V and 9 V of electricity of the vaporizer 100.

C. METHODS OF USE

In yet another aspect, a method is provided for administering an inhalable composition to a subject in need thereof, the method comprising providing the subject with: (a) the inhalable composition comprising caffeine, or a salt thereof, and a solvent selected from the group consisting of propylene glycol, glycerol, ethanol and a combination thereof; and (b) an apparatus for the pulmonary administration of the inhalable composition; wherein the method results in a pulmonary administration of at least 0.0001 mg of caffeine from the inhalable composition to the subject. In one embodiment, the method further comprises instructing the subject to inhale the inhalable composition from the apparatus.

In one embodiment of the method, the inhalable composition is any of the inhalable compositions described herein. For example, the inhalable composition may further comprise yerba mate leaf extract, huperizine, taurine, inositol, niacinamide, phenylalanine, citicoline, or a salt of any thereof, propylene glycol, glycerol, ethanol and water.

In one embodiment of the method, the inhalable composition comprises: about 3.8 wt % caffeine HCl, about 2.5 wt % yerba mate leaf extract, about 1×10⁻⁸ wt % huperizine, about 9.5 wt % taurine, about 9.5 wt % inositol, about 0.6 wt % niacinamide, about 9.5 wt % phenylalanine, about 7.6 wt % citicoline, about 9.5 wt % propylene glycol, about 9.5 wt % glycerol, and water.

In some embodiments of the method, about 1, 2, 3, 4, 5, 6, 7, 8, 9, 10, 11, 12, 13, 14, 15, 16, 17, 18, 19, 20, 25, 30, 35, 40, 45 or 50 mg, or an amount between any two of these values, of caffeine or a salt thereof is inhaled by the subject per inhalation (i.e., vape). Thus, in some embodiments of the method, about 0.0005 mg to about 10 mg of caffeine or a salt thereof is inhaled by the subject per inhalation. In some embodiments of the method, about 10 mg to about 20 mg of caffeine or a salt thereof is inhaled by the subject per inhalation. In some embodiments of the method, about 20 mg to about 30 mg of caffeine or a salt thereof is inhaled by the subject per inhalation. In some embodiments of the method, about 30 mg to about 40 mg of caffeine or a salt thereof is inhaled by the subject per inhalation. In some embodiments of the method, about 40 mg to about 50 mg of caffeine or a salt thereof is inhaled by the subject per inhalation.

In some embodiments of the method, the composition further comprises nicotine or a salt thereof. In some embodiments of the method, less than 1 mg of nicotine is provided to a subject per inhalation of any one of these compositions. For example, some embodiments of the method, at least about 1, 2, 3, 4, 5, 6, 7, 8, 9, 10, 11, 12, 13, 14, 15, 16, 17, 18, 19, 20, 25, 30, 35, 40, 45 or 50 μg, or an amount between any two of these values, of nicotine or a salt thereof, is provided to the subject per inhalation (i.e., vape).

In some embodiments of the method, the composition is inhaled from the apparatus as a vapor comprising liquid droplets. In some embodiments of the method, the droplets have an average diameter of about 0.5, 1, 2.5 10, or 20 microns, or a diameter between any two of these values.

In some embodiments of the method, the vapor is formed at about 250° F., 300° F., 350° F., 400° F., 450° F., 500° F., 550° F., or a temperature between any two of these values.

In one embodiment of the method, the apparatus is an electronic vaporizer, such as an electronic cigarette. In one embodiment of the method, the apparatus is any apparatus as described herein.

In another aspect, a method of treatment is provided, comprising: (a) aerosolizing any one of the inhalable compositions or formulations comprised of caffeine, or a salt thereof, as described herein, creating aerosolized droplets which are sufficiently small as to enter the alveolar ducts; (b) allowing a subject to inhale the aerosolized droplets of (a) thereby causing caffeine, or a salt thereof, to enter the patient's blood at air/blood diffusion membranes. In some embodiments, the method further comprises: (c) repeating (a) and (b) a plurality of times.

The present technology, thus generally described, will be understood more readily by reference to the following examples, which is provided by way of illustration and is not intended to limit the present technology.

D. EXAMPLES

Example 1. Preparation of an Exemplary Inhalable Formulation of Caffeine

The substances listed in Table 1 are combined to form "Inhalable Formulations A, B and C."

TABLE 1

| Substances | Formulation | | |
| --- | --- | --- | --- |
| | A | B | C |
| caffeine HCl | 100 mg | 200 mg | 300 mg |
| yerba mate leaf extract | 130 mg | 130 mg | 130 mg |
| huperzine A | 50 mcg | 50 mcg | 50 mcg |
| taurine | 500 mg | 500 mg | 500 mg |
| inositol | 500 mg | 500 mg | 500 mg |
| niacinamide | 30 mg | 30 mg | 30 mg |
| phenylalanine | 500 mg | 500 mg | 500 mg |
| citicoline | 400 mg | 400 mg | 400 mg |
| citric acid (*optional) | 200 mg | 200 mg | 200 mg |
| peppermint (*optional) | 200 mg | 200 mg | 200 mg |
| lemon or orange extract (*optional) | 200 mg | 200 mg | 200 mg |
| propylene glycol | 400 mg | 500 mg | 600 mg |
| vegetable glycerol | 600 mg | 500 mg | 400 mg |
| de-ionized water | 2,100 mg | 2,000 mg | 1,900 mg |

*subtract −200 mg of de-ionized water if necessary for cartridge fit

Example 2. Vaporization of Inhalable Caffeine Formulations

The substances listed in Table 2 are combined with solvent systems i-xi in Table 3 to form Inhalable Formulations D-N. Inhalable Formulations D-N are allowed to stand at room temperature for 24 hours and examined for signs of precipitation or emulsification. Inhalable Formulations D-N are then added to an electronic vaporizer (e.g., electronic cigarette) known in the art or as described herein. Each of Formulations D-N is separately vaporized in a quantity that simulates a "vape" i.e., the amount of vapor that will be inhaled by a subject from an electronic vaporizer. The resulting vapors are captured. The captured vapors are diluted with water, the caffeine is precipitated from solution, collected and quantified. It is contemplated that some or all of Formulations D-N will deliver at least 0.0001 mg of caffeine or a salt thereof per vape.

TABLE 2

| Substances | Amount |
| --- | --- |
| caffeine HCl | 200 mg |
| yerba mate leaf extract | 130 mg |
| huperzine A | 50 mcg |
| taurine | 500 mg |
| inositol | 500 mg |
| niacinamide | 30 mg |
| phenylalanine | 500 mg |
| citicoline | 400 mg |
| citric acid (*optional) | 200 mg |
| peppermint (*optional) | 200 mg |
| lemon or orange extract (*optional) | 200 mg |
| propylene glycol | * |
| vegetable glycerol | * |
| de-ionized water | 2,000 mg |

* propylene glycol + vegetable glycerol = 1,000 mg

TABLE 3

| Solvent System | Propylene Glycol | Vegetable Glycerol | Formulation * |
| --- | --- | --- | --- |
| i | 0 mg | 1,000 mg | D |
| ii | 100 mg | 900 mg | E |
| iii | 200 mg | 800 mg | F |
| iv | 300 mg | 700 mg | G |
| v | 400 mg | 600 mg | H |
| vi | 500 mg | 500 mg | I |
| vii | 600 mg | 400 mg | J |
| viii | 700 mg | 300 mg | K |
| ix | 800 mg | 200 mg | L |
| x | 900 mg | 100 mg | M |
| xi | 1,000 mg | 0 mg | N |

* Upon combination with the substances of Table 2.

Example 3. Single-Dose Application of Inhalable Caffeine Formulations

An electronic vaporizer (e.g., electronic cigarette) known in the art or described herein may be used to deliver single-bolus doses of Inhalable Composition B to healthy adults. A substantially uniform aerosol is created when the Inhalable Composition B solution is vaporized by the electronic vaporizer. The fine aerosol that is generated allows the deep-lung deposition needed to achieve rapid and efficient absorption of caffeine.

Methods: Eighteen healthy, adults are enrolled in a randomized, open-label, multiple-exposure study which is conducted in two parts. Two subjects are removed prior to Study Part 2 with sixteen subjects starting and completing Study Part 2. Subjects' ages may range, for example from about 19-41 years.

In Study Part 1, the tolerability and safety of Inhalable Formulation B is evaluated. In Study Part 2, subjects received one of three caffeine concentrations (from Formulations A, B and C), delivering various bolus caffeine lung doses. Measures of arterial caffeine plasma concentration and post-dosing alertness self-scores (over a 10-point scale) are made following a single inhalation of caffeine.

Results: It is anticipated that no clinically significant changes in safety measures will be noted following dosing (vital signs, ECG, spirometry, labs). Adverse events (AEs), if any, are expected to be mild or moderate and self-resolvable without medication.

Pharmacokinetics: Arterial plasma caffeine pharmacokinetics are contemplated to demonstrate a rapid onset ($T_{max}$=about 1 min) and substantial peak plasma concentrations. Maximum plasma concentrations ($C_{max}$) and area under the concentration-time curves (AUC) are contemplated to consistent with a trend toward dose proportionality.

Alertness: Patients are asked to rate their alertness on a scale of 0 to 10 pre- and post-dosing. Subjects are anticipated to report an increase in alertness post-dosing relative to pre-dosing. A mean increase in alertness from baseline can be calculated for all three dose levels.

Conclusions: It is contemplated that pulmonary administration of the inhalable formulations of caffeine, described herein, via an electronic vaporizer (e.g., electronic cigarette) known in the art or described herein will be safe and tolerable. The electronic vaporizer is expected to deliver inhaled caffeine with a PK profile that is consistent with the rapid delivery and absorption, and alertness in subjects is expected to increase post-dosing.

E. EQUIVALENTS

The present disclosure is not to be limited in terms of the particular embodiments described in this application. Many modifications and variations can be made without departing from its spirit and scope, as will be apparent to those skilled in the art. Functionally equivalent methods, processes and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, processes, reagents, compounds compositions or biological systems, which can of course vary. It is also to be understood that the terminology used herein is for the purpose of describing particular embodiments only, and is not intended to be limiting.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All processes described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

While certain embodiments have been illustrated and described, it should be understood that changes and modifications could be made therein in accordance with ordinary skill in the art without departing from the technology in its broader aspects as defined in the following claims.

What is claimed is:

1. A vaporizer comprising:
an atomizer coupled to a controller;

a cartridge comprising an inhalable composition;
wherein the inhalable composition comprises about 1 wt. % to about 10 wt. % of caffeine HCl and an active ingredient selected from the group consisting of: *Panax Ginseng* (*Aralia quinquefolia*), Gingko *Biloba* (*Ginkgo biloba* L.), Bitter Orange (*Citrus aurantium* L.), Cola-Nut (*Cola acuminate*), Guarana (*Paullinia cupana*), Natrum Carbonicum, Green Tea (*Camellia sinensis*), Cocoa Extract (*Theobroma cacao* L.), Licorice (*Glycyrrhiza glabra* L.), Natrum Carbonicum, Ginger (*Zingiber officinale* Rosc.), P57 Hoodia, Glucuronolac-tone, Yerba Mate (llex paraguensis St. Hil) *Garcinia Cambogia*, Hoodia *Gordonii*, Kelp, and Peppermint (Mentholum); and
wherein the inhalable composition has a mass median aerodynamic diameter (MMAD) between 0.5 and 5 microns; and
wherein the controller is configured to control activation of the atomizer to heat the inhalable composition and form vapes of one or more active ingredients of the inhalable composition that are inhalable via an opening by a subject.

2. The vaporizer of claim 1, wherein the inhalable composition comprises about 3.8 wt. % caffeine HCl.

3. The vaporizer of claim 1, wherein the inhalable composition comprises a water-miscible solvent selected from the group consisting of propylene, glycol, glycerol, ethanol and a combination thereof.

4. The vaporizer of claim 1, wherein the controller is further configured to limit an amount of inhalable composition the subject may inhale.

5. The vaporizer of claim 1, wherein the controller is further configured to cause the vaporizer to enter a refractory state for a predetermined amount of time after administration of one or more vapes.

6. The vaporizer of claim 1, wherein the controller is further configured to limit a number of vapes administered within a predetermined time window.

7. A vaporizer comprising:
an atomizer coupled to a controller;
a cartridge comprising an inhalable composition;
wherein the inhalable composition comprises one or more active ingredients of nicotine, or a salt thereof, about 1 wt. % to about 10 wt. % of caffeine HCl, and an active ingredient selected from a group consisting of: *Panax Ginseng* (*Aralia quinquefolia*), Gingko *Biloba* (*Ginkgo biloba* L.), Bitter Orange (*Citrus aurantium* L.), Cola-Nut (*Cola acuminate*), Guarana (*Paullinia cupana*), Natrum Carbonicum, Green Tea (*Camellia sinensis*), Cocoa Extract (*Theobroma cacao* L.), Licorice (*Glycyrrhiza glabra* L.), Natrum Carbonicum, Ginger (*Zingiber officinale* Rosc.), P57 Hoodia, Glucuronolac-tone, Yerba Mate (llex paraguensis St. Hil) *Garcinia Cambogia*, Hoodia *Gordonii*, Kelp, and Peppermint (Mentholum); and
wherein the inhalable composition has a mass median aerodynamic diameter (MMAD) between 0.5 and 5 microns; and
wherein the controller is configured to control activation of the atomizer to heat the inhalable composition and form vapes of the one or more active ingredients of the inhalable composition that are inhalable via an opening by a subject.

8. The vaporizer of claim 7, wherein the inhalable composition is formulated to provide less than 1 mg of the nicotine, or salt thereof, to the subject per inhalation.

9. The vaporizer of claim 7, wherein the inhalable composition comprises between 0.1 wt. % to about 5 wt. % nicotine, or salt thereof.

10. The vaporizer of claim 7, wherein the inhalable composition comprises about 3.8 wt. % caffeine HCl.

* * * * *